United States Patent [19]

Tsuji et al.

[11] Patent Number: 5,122,354
[45] Date of Patent: Jun. 16, 1992

[54] HISTIDINE-HYDROGEN PEROXIDE ADDUCT AND PROCESS FOR PREPARING SAME

[75] Inventors: Kuniro Tsuji, Shizuoka; Haruo Nukaya, Shimizu; Yasuhiro Kanaya, Fushi, all of Japan

[73] Assignee: Tokai Denka Kogyo Kabushiki Kaisha, Tokyo, Japan

[21] Appl. No.: 556,029

[22] Filed: Jul. 20, 1990

[30] Foreign Application Priority Data

Jul. 20, 1989 [JP] Japan ................. 1-185872

[51] Int. Cl.⁵ .......................... C01B 15/037
[52] U.S. Cl. ................. 423/272; 252/186.29; 423/266
[58] Field of Search .......... 548/344; 252/186.29, 252/700; 423/266, 272, 584, 587

[56] References Cited

U.S. PATENT DOCUMENTS

| | | | |
|---|---|---|---|
| 1,153,985 | 9/1915 | Weber | 423/584 |
| 3,325,417 | 6/1967 | Rauhut | 252/700 |
| 3,480,557 | 11/1969 | Shiraeff | 423/272 |
| 3,755,185 | 8/1973 | Waldmann et al. | 423/272 |

FOREIGN PATENT DOCUMENTS 14502 of 1911 United Kingdom ................ 423/584

OTHER PUBLICATIONS

Chemical Abstract 70:75,383f (1969).
Chemical Abstract 111:235,672v (1989).

*Primary Examiner*—Jeffrey E. Russel
*Attorney, Agent, or Firm*—Scully, Scott, Murphy & Presser

[57] ABSTRACT

A crystallized, stable histidine-hydrogen peroxide adduct intermolecular-bonded at 1:1 ratio is provided.

4 Claims, 1 Drawing Sheet

HISTIDINE-HYDROGEN PEROXIDE ADDUCT AND PROCESS FOR PREPARING SAME

BACKGROUND OF THE INVENTION

The present invention relates to a novel and stable hydrogen peroxide adduct and a process for preparing same. Particularly, the present invention is concerned with a crystallized, stable histidine-hydrogen peroxide adduct and a process for preparing same.

One method for crystallizing hydrogen peroxide which is liquid is to make hydrogen peroxide into an adduct. Adducts of hydrogen peroxide are broadly classified into the following two according to liquid properties of aqueous solutions thereof. The two are those whose aqueous solutions exhibit alkalinity such as sodium percarbonate and sodium perborate and those whose aqueous solutions exhibit acidity such as urea peroxide.

Sodium percarbonate and sodium perborate are used widely as oxygen type bleaches, pipe detergents, etc.

Urea peroxide is used as a decoloring agent for the treatment of hair before hair dyeing or as an oxidizing agent for dyes.

They are each prepared by contacting an aqueous solution of sodium carbonate, sodium metaborate, or urea, with hydrogen peroxide to crystallize sodium percarbonate, sodium perborate or urea peroxide.

However, these conventional hydrogen peroxide adducts involve the following problems.

(1) Since aqueous solution of sodium parcarbonate and sodium perborate are alkaline, hydrogen peroxide is apt to decompose and so they are unstable.

(2) Aqueous solutions of sodium percarbonate and sodium perborate erode proteinaceous materials such as silk and wool because of their strong alkalinity, so they are not only unsuitable for the bleaching of those materials but also involve the danger of injuring the human body.

(3) As to urea peroxide, an aqueous solution thereof exhibits acidity.

(4) It is difficult to preserve sodium percarbonate, sodium perborate and urea peroxide over a long period under high temperature and high humidity conditions because they are easily decomposed by the moisture contained in air.

(5) Since urea peroxide is easily decomposed rapidly by shock or heat, it is necessary to handle it carefully.

It is the object of the present invention to provide a novel hydrogen peroxide adduct free of the above-mentioned problems.

SUMMARY OF THE INVENTION

Having made extensive studies for overcoming the above-mentioned problems, the present inventor found a 1:1 inter-molecular-bounded adduct of histidine and hydrogen peroxide affords stable crystals and is superior in the preservation stability of the crystals and that an aqueous solution thereof is substantially neutral, superior in stability, etc. and useful as various agents in which hydrogen peroxide and peroxides are generally utilized such as a bleaching agent for fibers and pulps, an oxidizing or reducing agent in the organic or inorganic chemical industry, and a sterilizer for foods, packages, etc. In this way the present inventor accomplished the present invention.

More specifically, the present invention resides in a crystallized, stable histidine-hydrogen peroxide adduct represented by the following general formula (I) wherein histidine and hydrogen peroxide are inter-molecular-bonded at 1:1 ratio:

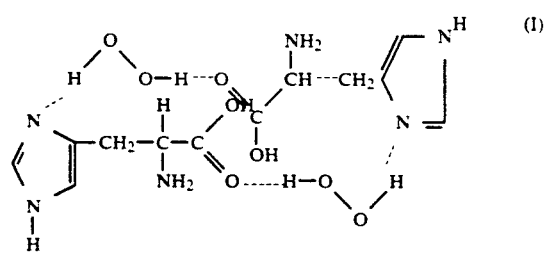

The histidine-hydrogen peroxide adduct of the present invention is prepared by contacting histidine with hydrogen peroxide in an aqueous medium.

DETAILED DESCRIPTION OF THE INVENTION

Figure 1:
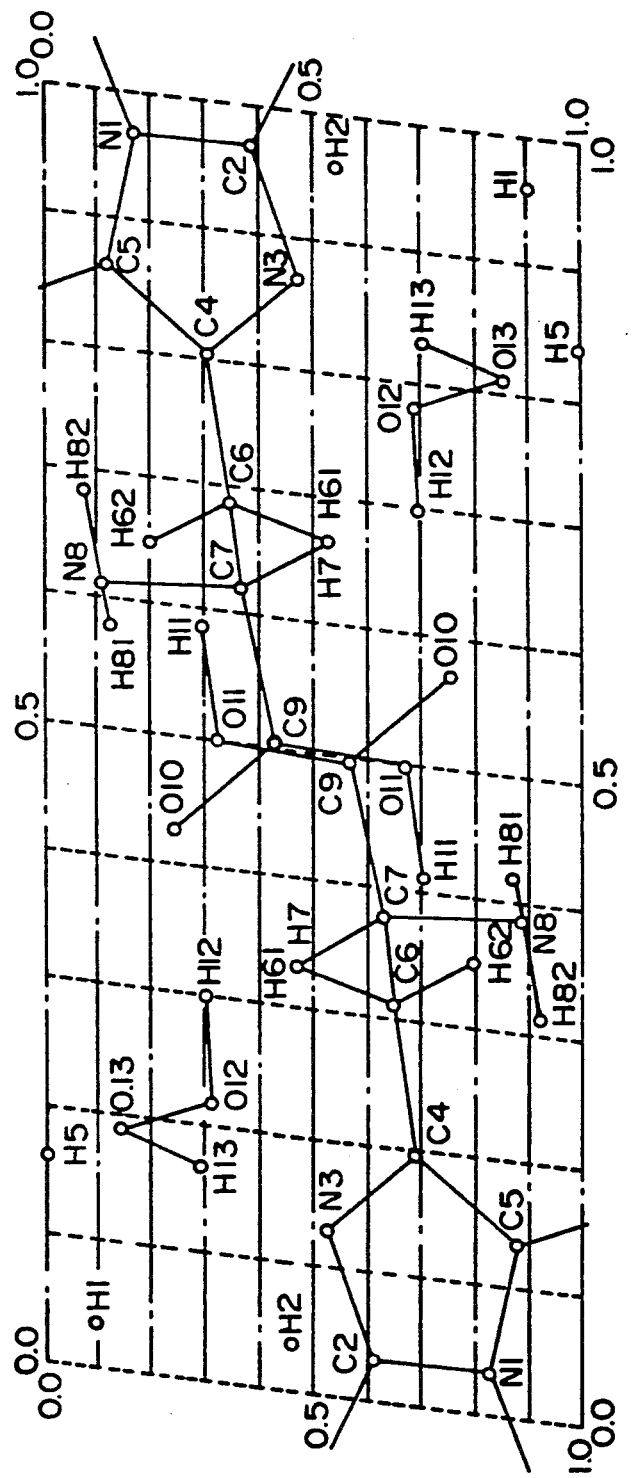
FIG. 1 is an explanatory view of a molecular structure based on X-ray analysis of the histidine-hydrogen peroxide adduct of the present invention.

Preperably, the adduct of the present invention is prepared by mixing water and histidine to form a slurry, adding hydrogen peroxide to the slurry in an amount of usually 1 to 1.5 equivalents, followed by stirring. Room temperature or thereabout is sufficient as the reaction temperature.

As a result of X-ray analysis the crystalline histidine-hydrogen peroxide adduct thus prepared proved to have such a chemical structure through hydrogen bonds as shown by the general formula (I).

The crystalline histidine-hydrogen peroxide adduct provided according to the present invention is stable even when allowed to stand for half a year in air, high in thermal stability, and is also highly stable under high temperature and high humidity conditions, and an aqueous solution thereof is substantially neutral, capable of overcoming all of the problems encountered in the prior art.

Application of the histidine-hydrogen peroxide adduct thus prepared to various uses of solid hydrogen peroxide can be expected, such as, for example, a household bleach, an oxygen source for medical use, and a sterilizer. Also as to decomposition products thereof, there are produced only histidine and water, so it is not necessary to consider secondary pollutions.

The present invention will be described below in terms of a working examples thereof, but it is to be understood that the invention is not limited thereto.

EXAMPLE 21 g of histidine and 189 g of water were placed in a 300 ml conical beaker. To the resultant slurry was added 11.5 g of 60% aqueous hydrogen peroxide little by little under stirring. After 20 minutes of stirring, the slurry was filtered off and the resultant crystals were washed with cold methanol, then dried to afford 2.08 g (82%) of a histidine-hydrogen peroxide adduct. The decomposition temperature of the adduct was found to be 146.8° C.

This product was subjected to X-ray analysis for structural analysis. The results are as shown in FIG. 1, which is an explanatory view of a molecular structure of the compound produced.

What is claimed is:

1. A solid crystal histidine-hydrogen peroxide adduct represented by the general formula (I):

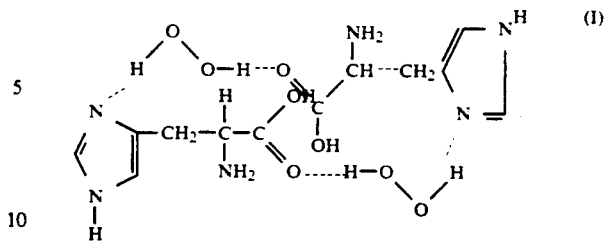

2. A process for preparing the histidine-hydrogen peroxide adduct of claim 1, comprising contacting histidine with hydrogen peroxide by gradually adding an aqueous hydrogen peroxide solution to an aqueous solution of histidine at a temperature and for a period of time effective for the formation of said adduct.

3. The process of claim 2 wherein the ratio of hydrogen peroxide to histidine is 1.0 to 1.5 equivalents to 1.0 equivalent.

4. The process of claim 2 further comprising passing the mixture of solutions through a filter to recover the adduct.

* * * * *

UNITED STATES PATENT AND TRADEMARK OFFICE
CERTIFICATE OF CORRECTION

PATENT NO. : 5,122,354

DATED : June 16, 1992

INVENTOR(S) : Kuniro Tauji, et al.

It is certified that error appears in the above-identified patent and that said Letters Patent is hereby corrected as shown below:

Column 2, lines 5-14, and Column 4, lines 1-12,

Claim 1: " 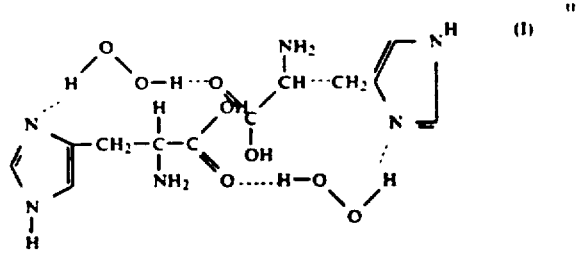 "

UNITED STATES PATENT AND TRADEMARK OFFICE
CERTIFICATE OF CORRECTION

PATENT NO.  : 5,122,354
DATED       : June 16, 1992
INVENTOR(S) : Kuniro Tauji, et al.

It is certified that error appears in the above-identified patent and that said Letters Patent is hereby corrected as shown below:

should read as

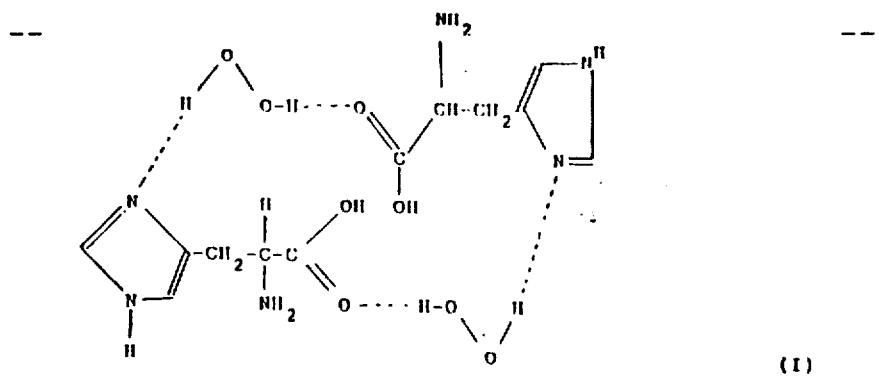

Signed and Sealed this

Second Day of November, 1993

Attest:

BRUCE LEHMAN

Attesting Officer     Commissioner of Patents and Trademarks